(12) United States Patent
Ahn et al.

(10) Patent No.: US 6,214,868 B1
(45) Date of Patent: Apr. 10, 2001

(54) METHOD FOR PREVENTING OR TREATING CORONARY RESTENOSIS WITH CATECHIN

(75) Inventors: Hee-Yul Ahn, Chungcheongbuk-do; Jong-Bum Park, Kyungki-do; Yeo-Pyo Yun, Chungcheongbuk-do; Myeong-Chan Cho, Chungcheongbuk-do; Young-Gyu Kim, Chungcheonbuk-do, all of (KR)

(73) Assignee: Sam-A Pharm. Co., Ltd., Kyungki-do (KR)

( * ) Notice: Subject to any disclaimer, the term of this patent is extended or adjusted under 35 U.S.C. 154(b) by 0 days.

(21) Appl. No.: 09/567,701

(22) Filed: May 10, 2000

(30) Foreign Application Priority Data

Feb. 29, 2000 (KR) .................................................. 00-10132

(51) Int. Cl.$^7$ ...................................................... A61K 31/35
(52) U.S. Cl. ................................................................ 514/456
(58) Field of Search ............................................... 514/456

(56) References Cited

U.S. PATENT DOCUMENTS

| 5,527,552 | * | 6/1996 | Todd, Jr. .............................. 426/541 |
| 5,804,168 | * | 9/1998 | Murad .................................. 424/59 |
| 6,096,359 | * | 8/2000 | Bombardelli et al. ............... 426/428 |

* cited by examiner

*Primary Examiner*—Raymond Henley, III
(74) *Attorney, Agent, or Firm*—Rosenman & Colin, LLP

(57) ABSTRACT

A coronary restenosis in a mammal can be prevented or treated by administering an effective amount of a catechin thereto.

9 Claims, 12 Drawing Sheets

500μm

METHOD FOR PREVENTING OR TREATING CORONARY RESTENOSIS WITH CATECHIN

FIELD OF THE INVENTION

The present invention relates to a method for preventing or treating coronary restenosis by way of administering a green tea catechin.

BACKGROUND OF THE INVENTION

Green tea contains astringent tea tannin in an amount of 10% to 15%. Tea tannin is comprised of polyphenols which are catechins represented by epigallocatechin-3-gallate (EGCG), epigallocatechin(EGC), epicatechin-3-gallate (ECG), epicatechin(EC), gallocatechin-3-gallate(GCG), gallocatechin(GC) and catechin(C).

Catechins have been reported to have: peroxy-lipid-inhibiting activity(Kinura et al., *J. Jpn. Soc. Nutr. Food Sci.*, 37, 223–232 (1984)); antioxidant activity for fat and fatty oil(Okuda, T. et al., *Chem. Pharmacol. Bull.*, 31, 1625–1631 (1983)); antihypertensive activity; antifungal activity; antihyperglycemic activity; hypercholesteremia-inhibiting activity; antiulcerative activity; and anticancer activity (Fukuyo, M. et al., *J. Jpn. Soc. Nutr. Food Sci.*, 39, 495–500 (1986)).

Percutaneous transluminal coronary angioplasty (PTCA) has been widely practiced for treating ischemic cardiac diseases. However, post-PTCA coronary restenosis occurs at an unacceptably high frequency of 30% to 50% (Popma, J. J. et al., *Circulation*, 84, 1426–1436 (1991); and Gruentzig, A. R. et al., *N Engl J Med*, 316, 1127–1132 (1987)).

According to the clinical and experimental studies, restenosis proceeds via the steps of: elastic recoiling; thrombogenesis and organization of the connective tissue; intimal hyperplasia; and vessel wall remodeling(Mintz, G. S. et al., *Circulation*, 94, 35–43 (1996); Kagan, S. A., *Surg Clin North Am*, 78, 481–500 (1998); McBride, W. et al., *N Engl J Med*, 318, 1734–1737 (1988); Califf, R. M. et al., *J Am Coll Cardiol*, 17, 2B–13B (1991); Schwartz, S. M. et al., *Mayo Clin Proc*, 68, 54–62 (1993); and Schwartz, R. S. et al., *Mayo Clin Proc*, 68, 54–62 (1993)). The intimal hyperplasia, in particular, is caused by the growth and movement of vascular smooth muscle cells(VSMCs) coupled with the formation of an extracellular matrix, the VSMCs being induced by the combined actions of materials released from damaged blood vessels and growth-stimulating materials produced by the activated platelet.

It has been reported that stent enthesis into the coronary artery effectively prevents elastic recoil and vessel wall remodeling, thereby lowering the frequency of restenosis to about 10%(Serruys, P. W. et al., *N Engl J Med*, 331, 496–501 (1988); and Fischman, D. L. et al., *N Engl J Med*, 331, 496–501 (1994)). However, the stent enthesis may promote a serious case of intimal hyperplasia, to thereby generate in-stent restenosis.

To prevent coronary restenosis, therefore, various attempts have made using advanced PTCA equipment, e.g., atherectomy, angioplasty using a laser, rotablator, angioplasty of the coronary vessel using a cutting balloon, and irradiative treatments. Further, systemic or local drug therapies have been attempted using an antiplatelet agent, an antithrombotic agent, a vasodilator, a cytostatic, a lipid metabolism-improving agent or an antioxidant(Califf, R. M. et al., *J Am Coll Cardiol*, 17, 2B–13B (1991); Popma, J. J. et al., *Circulation*, 84, 1426–1436 (1991); and Herrman, J. P. R. et al., *Drugs*, 46, 18–22 (1991)); and also attempts have been made to employ a gene therapy(De Young, M. B. et al., *Circ Res*, 82, 306–313 (1998); Baek, S. H. et al., *Circ Res*, 82, 295–305 (1998); Libby, P., *Circ Res*, 82, 404–406 (1998); Nikol, S., *Heart*, 78, 426–428 (1997); Morishita, R. et al., *Circ Res*, 82, 1023–1028 (1998); and George, S. J. et al., *Hum Gene Ther*, 9, 867–877 (1998)). Among these, the systemic drug therapy, which was found to be effective in animal tests, has failed to prevent coronary restenosis in clinical tests due to the occurrence of undesirable side effects. As restenosis occurs at a local PTCA site of coronary artery, a local drug therapy which delivers a high concentration of a drug to the site is more desirable than a systemic drug therapy. For such a local drug delivery, there have recently been developed various methods employing such devices as a double balloon catheter, a dispatch, a microporous balloon(Brieger D. et al., *Cardiovasc Res*, 35, 405–413 (1997); Yla-Herttuala S., *Curr Opin Lipidol*, 8, 72–76 (1997); and Laitinen, M. et al., *Pharmacol Res*, 37, 251–254 (1998)), a slow-release microsphere and a drug-coated stent. However, these methods are limited in their effectiveness. Therefore, there has existed a need to develop an effective method for preventing coronary restenosis after PTCA.

SUMMARY OF THE INVENTION

Accordingly, it is a primary object of the present invention to provide an effective method for preventing or treating coronary restenosis.

In accordance with one aspect of the present invention, there is provided a method for preventing or treating coronary restenosis which comprises administering an effective amount of a catechin to a subject.

BRIEF DESCRIPTION OF THE DRAWINGS

The above objects and features of the present invention will become apparent from the following description of preferred embodiments taken in conjunction with the accompanying drawings, wherein.

DETAILED DESCRIPTION OF PREFERRED EMBODIMENTS

Figure 1:
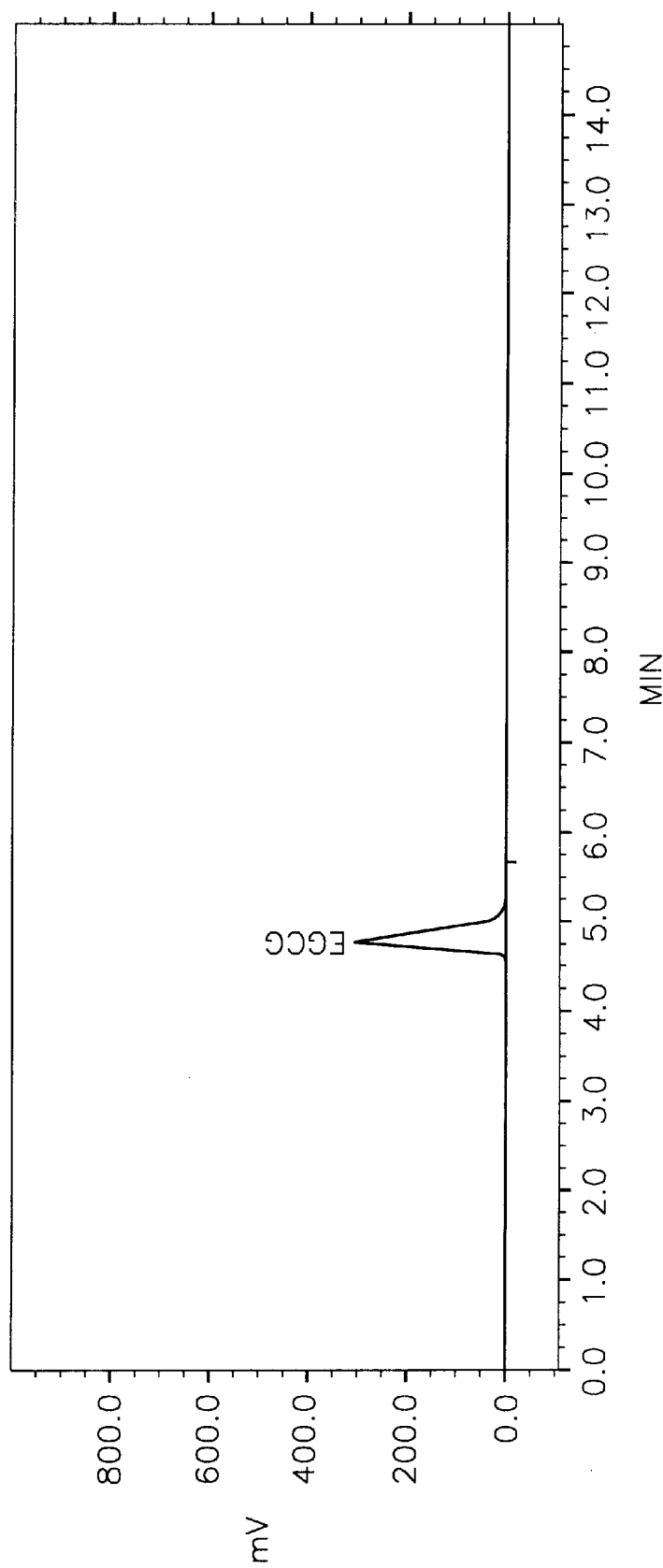
FIG. 1 presents a HPLC scan of EGCG.
Figure 2:
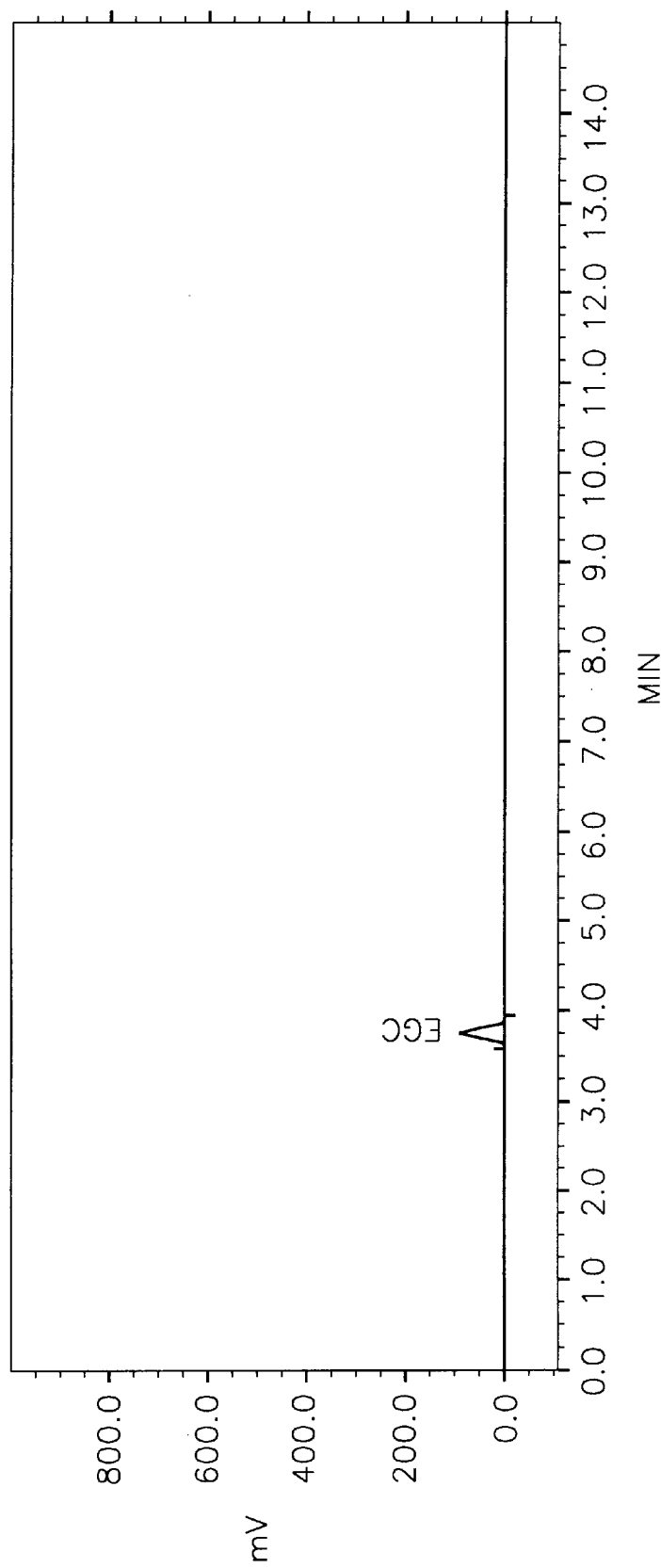
FIG. 2 provides a HPLC scan of EGC.
Figure 3:
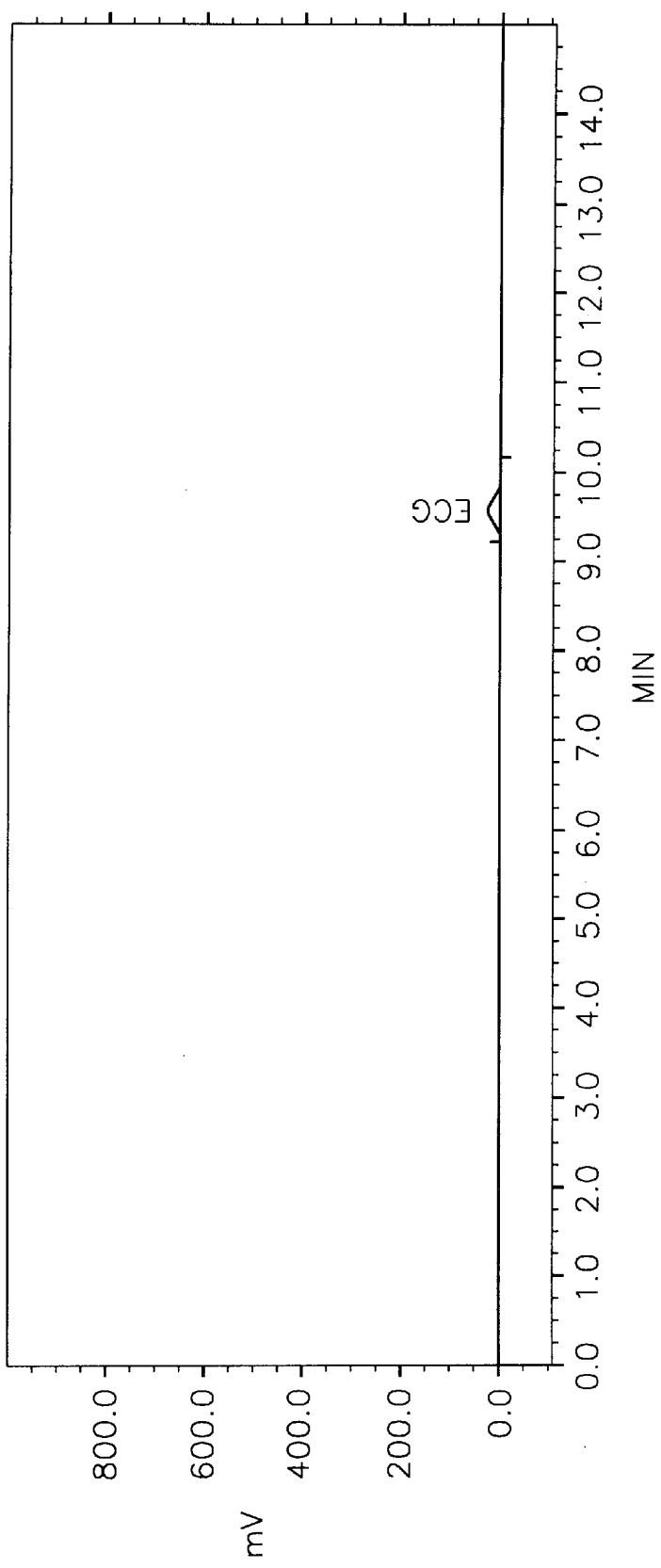
FIG. 3 offers a HPLC scan of ECG.
Figure 4:
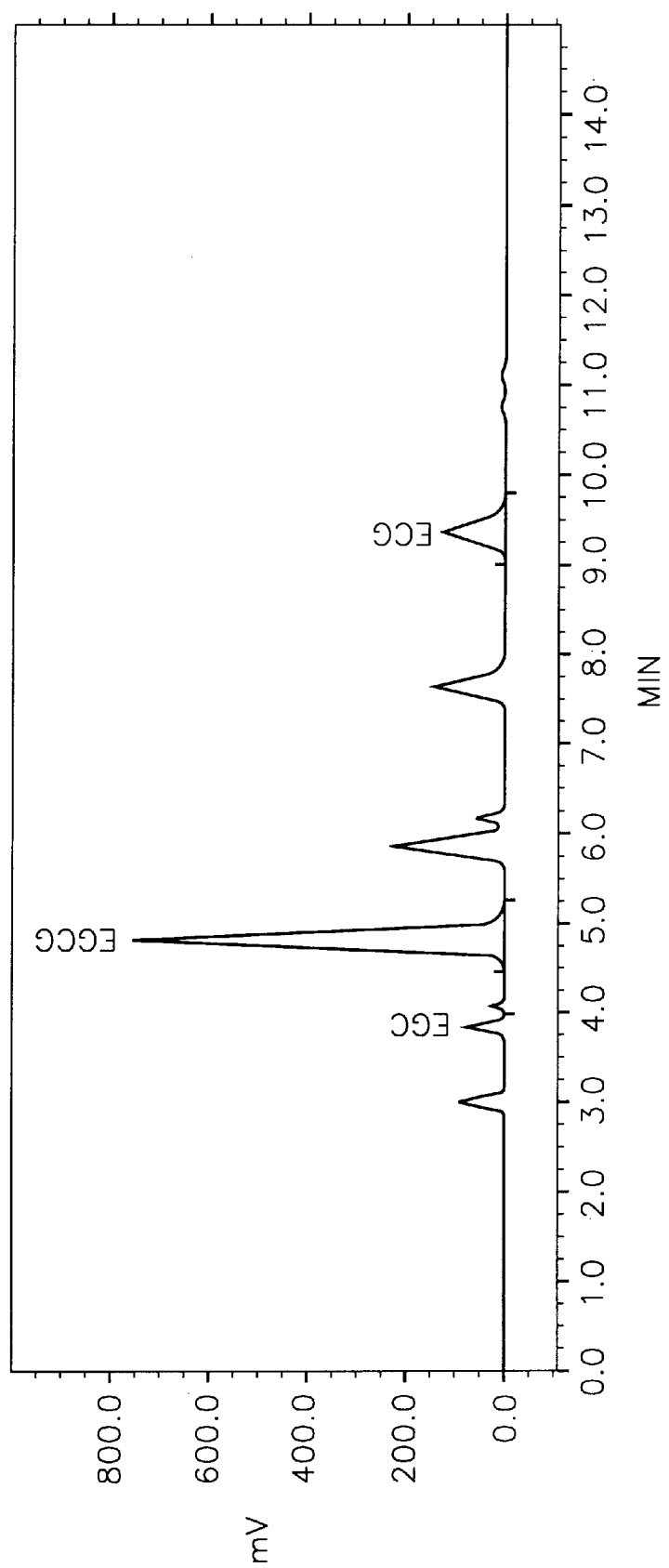
FIG. 4 illustrates a HPLC scan of a green tea extract.

The catechin which may be used as an active ingredient in the present invention includes a green tea extract containing catechins(designated GTC) which are represented by epigallocatechin-3-gallate(EGCG), epigallocatechin(EGC), epicatechin-3-gallate(ECG), epicatechin(EC), gallocatechin-3-gallate(GCG), gallocatechin(GC) and catechin(C).

The term "GTC" which is used in the present specification shall mean an extract obtained from green tea which comprises varying amounts of EGCG, ECG, EGC, EC, GCG and C, together with other components, e.g., caffeine. A GTC preferably has a total catechin content of 80% by weight or more, and more preferred is a GTC having an EGCG content of 25% or more based on the amount of the total catechins. Most preferred is a GTC which comprises EGCG ranging from 25 to 85% by weight, EGC ranging from 6 to 20% by weight and ECG ranging from 2 to 15% by weight, based on the amount of the total catechins.

A GTC is prepared from green tea in accordance with any of the conventional extraction methods, e.g., those disclosed in Korean Patent No. 97-11555, EP Raid-Open No. 547370 A2, JP Raid-Open Nos. 2-22755 and 7-179353 and U.S. Pat. No. 5,107,000. A typical extraction method comprises extracting green tea leaves with water or a mixture of water and a lower alcohol; filtering and/or centrifuging the extract to remove nonpolar materials; and subjecting the filtrate or the supernatant to column chromatography. An alternative extraction method comprises extracting green tea leaves with ethanol; concentrating the extract under a reduced pressure; diluting the concentrate with water; centrifuging the diluted solution to precipitate solid materials; washing the supernatant with chloroform; extracting the aqueous layer with an organic solvent, e.g., ethyl acetate; and concentrating and drying the organic fraction under a reduced pressure. One(1) g of the GTC thus obtained corresponds to 10 g of dried green tea leaves.

Catechins are active in inhibiting the growth of VSMCs and neointimal formation. Therefore, catechins may be used for preventing or treating coronary restenosis which occurs after angioplasty of coronary artery using a balloon, stent enthesis, coronary artery bypass graft or arteriovenous shunt. Catechins are safe as attested by the long history of green tea consumption as well as by the results of acute toxicity tests which show no toxicity at a GTC dosage of 5 g/kg or less.

In practicing the present invention, a GTC or its active ingredient may be administered in combination with pharmaceutically acceptable carriers. A pharmaceutical formulation suitable for use in the present invention may be prepared in accordance with any of the conventional procedures. In preparing the formulation, the active ingredient is preferably admixed or diluted with a carrier, or enclosed within a carrier which may be in the form of a capsule, sachet or other container. When the carrier serves as a diluent, it may be a solid, semi-solid or liquid material acting as a vehicle, excipient or medium for the active ingredient. Thus, the formulations may be in the form of a tablet, pill, powder, sachet, elixir, suspension, emulsion, solution, syrup, aerosol, soft and hard gelatin capsule, sterile injectable solution, sterile packaged powder and the like.

Examples of suitable carriers, excipients, and diluents are lactose, dextrose, sucrose, sorbitol, mannitol, starches, gum acacia, alginates, gelatin, calcium phosphate, calcium silicate, cellulose, methyl cellulose, microcrystalline cellulose, polyvinylpyrrolidone, water, methylhydroxybenzoates, propylhydroxybenzoates, talc, magnesium stearate and mineral oil. The formulations may additionally include fillers, anti-agglutinating agents, lubricating agents, wetting agents, flavoring agents, emulsifiers, preservatives and the like. The compositions of the invention may be formulated so as to provide quick, sustained or delayed release of the active ingredient after their administration to a mammal by employing any of the procedures well known in the art.

The pharmaceutical formulation of the present invention can be administered via various routes including oral, transdermal, subcutaneous, intravenous and intramuscular introduction. In case of human, a typical daily dose of catechin may range from about 6 to 20 mg/kg body weight and can be administered in a single dose or in divided doses.

However, it should be understood that the amount of the active ingredient actually administered ought to be determined in light of various relevant factors including the condition to be treated, the chosen route of administration, the age, sex and body weight of the individual patient, and the severity of the patient's symptom; and, therefore, the above dose should not be intended to limit the scope of the invention in any way.

The following Examples are intended to further illustrate the present invention without limiting its scope.

Further, percentages given below for solid in solid mixture, liquid in liquid, and solid in liquid are on a wt/wt, vol/vol and wt/vol basis, respectively, unless specifically indicated otherwise.

REFERENCE EXAMPLE 1

Preparation of GTC 1,000 g of green tea(*Theae sinensis* L., Theaceae-var. bohea(yabugida), Geju-do of Republic of Korea) was extracted first with 10 l of 70% ethanol at about 87° C. for 3 hours and then with 5 l of the same solvent. The combined extract was concentrated to a volume of 1 l with a vacuum rotary dryer. About 2 l of water was added to the concentrate, and then, centrifuged at 14,000 rpm for 20 minutes to separate solid materials. The supernatant was washed with a 1.2-fold volume of chloroform and the water layer was extracted four times, each with a 1.2-fold volume of ethyl acetate. The ethyl acetate fractions were combined and the solvent was evaporated under a reduced pressure. The residue was dissolved in a small amount of water and freeze-dried to obtain a GTC powder.

REFERENCE EXAMPLE 2

Quantitative Analyses of GTC (1) Quantitative analysis of total catechin content of GTC To 25 mg of the GTC powder obtained in Reference Example 1, 80 ml of hot water was added, and then the resulting mixture was kept in a water bath maintained at 80° C. for 30 minutes. The resulting mixture was cooled to room temperature and then water was added thereto to a final volume of 100 ml. The resulting mixture was filtered. The first 20 ml filtrate was discarded and the remaining filtrate was used as a sample solution in the following procedures.

Placed in each of two 25 flasks were 5 ml water and 5 ml of the sample solution, and 5 ml of ferrous tartrate reagent and phosphate buffered solution(PBS) were sequentially added thereto to a final volume of 25 ml. The resulting solution was mixed thoroughly. The ferrous tartrate reagent was prepared by dissolving 0.1 g of ferrous sulfate(7 hydrate) and potassium tartrate in water to a final volume of 100 ml, and the PBS was prepared by mixing 0.066 M dibasic sodium phosphate and 0.66 M monobasic potassium phosphate and adjusting pH to 7.5.

The optical density of the mixture thus obtained was measured at 540 nm and its catechin concentration was assessed based on a calibration curve obtained using optical densities of standard solutions containing various concentrations of ethyl gallate($C_9H_{10}O_5$, M.W.:198.17, Tokyo Kasei Kogyo Co., LTD). The catechin content of the sample was then determined according to the following formula:

Content(%)=C×1.5(100/Weight of Sample(mg))×100 wherein C is the concentration(mg/ml) of ethyl gallate deduced from the calibration curve; and the coefficient 1.5 represents the optical density of 1 mg of ethyl gallate.

The above analysis showed that the GTC contained about 88%(w/w) catechin. Other analysis of the GTC powder revealed that it contained 1%(w/w) caffeine; 4%(w/w) water; and about 7% ash.

(2) Quantitative analyses of EGCG, EGC and ECG contents of GTC 25 mg of the GTC powder obtained in Reference Example 1 was placed in a 50 ml brown flask, and a mixture of methanol and 6% acetic acid(15:85(v/v)), a moving phase solvent, was added thereto to a final volume of 50 ml to obtain a sample solution. Meanwhile, standard solutions were prepared by placing 2 or 3 mg each of EGCG, EGC and ECG(having purities of 95% or more, 98% or more and 98% or more, respectively, Sigma) in a 25 ml brown flask and adding thereto the moving phase solvent to a final volume of 25 ml. 3 ml portions of the sample and standard solutions were subjected to HPLC, as follows:

<HPLC>

Instrument: HP 1050 series(Hewlett-Packard)

Separation Column: Hypersil BDS C18(250×4 mm, 5 μm)

Temperature: 40° C.

Wavelength: 280 nm

Moving Phase: a mixture of methanol and 6% acetic acid(15:85(v/v))

Retaining time: 15 minutes

HPLC scans of EGCG, EGC, ECG standard solutions and the GTC sample solution are shown in FIGS. 1, 2, 3 and 4, respectively.

The EGCG, EGC and ECG contents of the sample were determined using the following formula:

Content(%)=Concentration(mg/ml) of Sample Solution×(Peak Area of Sample Solution/Peak Area of Standard Solution)×(50/ Amount(mg) of Sample)×Purity(%) of the standard It was thus found that the GTC powder contained 37.5% (w/w) EGCG, 12.5% (w/w) EGC, 5.7% (w/w) ECG based on the total amount of catechins, the balance representing other catechins.

REFERENCE EXAMPLE 3

Primary Culture of Rat VSMCs 7-week-old Sprague-Dawley male rats(Korean Experimental Animal Center Ltd.) and 12- to 14-week-old Fisher 344 male rats(Charles River, Japan) were used in the experiment. Each rat was suffocated with $CO_2$, and its chest was disinfected and incised to remove the arteriae aorta. All operative apparatus and glass articles were autoclaved and all operations were conducted on a clean bench. The arteriae aorta was dipped in physiological salt solution(PSS) and its adipose tissues were removed. The resulting arteriae aorta was treated with 0.2% collagenase in an incubator maintained at 37° C. for 30 minutes. Its endothelium and adventitia were removed and the resulting arteriae aorta was ground up. A complete DMEM (DMEM containing 10% FBS, an antibiotic and glutamine) containing 0.2% collagenase was added thereto and the resulting mixture was kept at 37° C. for 4 hours while shaking with an orbital shaker.

The resulting mixture was centrifuged at 1,500×g for 5 minutes to remove the collagenase and the cell precipitate was suspended in an appropriate amount of complete DMEM. The cell suspension was divided into culture dishes and cultured in an incubator maintained 37° C. and 5% $CO_2$.

The cell number was determined by adding trypan blue to an aliquot of the culture and counting the cells under a microscope with a hemocytometer.

In the following Examples, values were represented in the form of mean ± standard deviation, and the significance thereof was tested in accordance with the unpaired student' t-test. Each experiment was repeated three times or more and a result having a P value of less than 0.05 is considered to be statistically significant.

EXAMPLE 1

Acute Toxicity Test of GTC

To each of 16 6- to 7-week-old beegles(8 males each weighing 7 to 9 kg and females each weighing 6 to 8 kg), the GTC obtained in Reference Example 1 was orally administered at a various dose ranging from 0.2 to 5 g/kg. None of the test animals died within 24 hours.

EXAMPLE 2

Inhibition of VSMC Growth by GTC

To examine the VSMC growth-inhibiting activity of GTC, a DNA incorporation test using $^3$H-thymidine was conducted as follows:

25,000 VSMCs obtained in Reference example 3 were distributed to the wells of a 24-well plate and cultured for 24 hours. The wells were washed twice with a serum-free medium, Hunger medium(Gibco), and fresh Hunger medium was added thereto. 1, 10, 30 and 100 μg/ml of GTC obtained in Reference Example 1 were respectively added to designated wells, and cultured for 24 hours to fix the cell cycle at $G_0$ stage. Each culture was washed with PBS, and then treated with Hunger medium containing 50 ng/ml PDGF-BB for 20 hours to induce cell division. 10 μl of $^3$H-thymidine solution(1–2 μCi/ml) was added to each well and then the resulting culture was incubated for 4 hours in an incubator maintained at 37° C. and 5% $CO_2$. The medium was discarded to remove unreacted $^3$H-thymidine and the resulting well was washed three times with 500 μl of ice-cold PBS. 500 μl of 10% TCA was added to each well and the resulting mixture was kept on ice for 20 minutes. Each well was washed three times with TCA and then three times with 500 μl of an ethanol-diethyl ether(1:1) mixture. 250 μl of 0.5 M NaOH was added to each well and the resulting mixture was kept on ice for 30 minutes. A 50 μl portion of the resulting reaction mixture was subjected to protein quantification. Further, a 100 μl portion of the resulting reaction mixture was added to 5 ml of a cocktail solution to measure the radioactivity, thereby determining the amount of $^3$H-thymidine incorporated into the cell. The procedure was repeated without the GTC treatment to obtain a control.

Further, to examine the VSMC growth-inhibiting activity of GTC in the absence of PDGF-BB, the above procedure was repeated without the PDGF-BB treatment. The results are shown in Tables I and II, and FIGS. 5A and 5B.

TABLE I

Effect of GTC on VSMC growth in the presence of PDGF-BB

|  | Control | GTC(μg/ml) | | | |
| --- | --- | --- | --- | --- | --- |
|  |  | 1 | 10 | 30 | 100 |
| ³H-thymidine incorporation (cpm/μg protein) | 1,363.4 ±158.5 | 495.4 ±27.9 | 93.5 ±11.0 | 68.8 ±5.2 | 7.2 ±3.6 |

TABLE II

Effect of GTC on VSMC growth in the absence of PDGF-BB

|  | Control | GTC(μg/ml) | | | |
| --- | --- | --- | --- | --- | --- |
|  |  | 1 | 10 | 30 | 100 |
| ³H-thymidine incorporation (cpm/μg protein) | 303.9 ±45.1 | 249.6 ±37.0 | 99.7 ±14.2 | 112.1 ±20.4 | 77.4 ±12.3 |

Figure 5A:
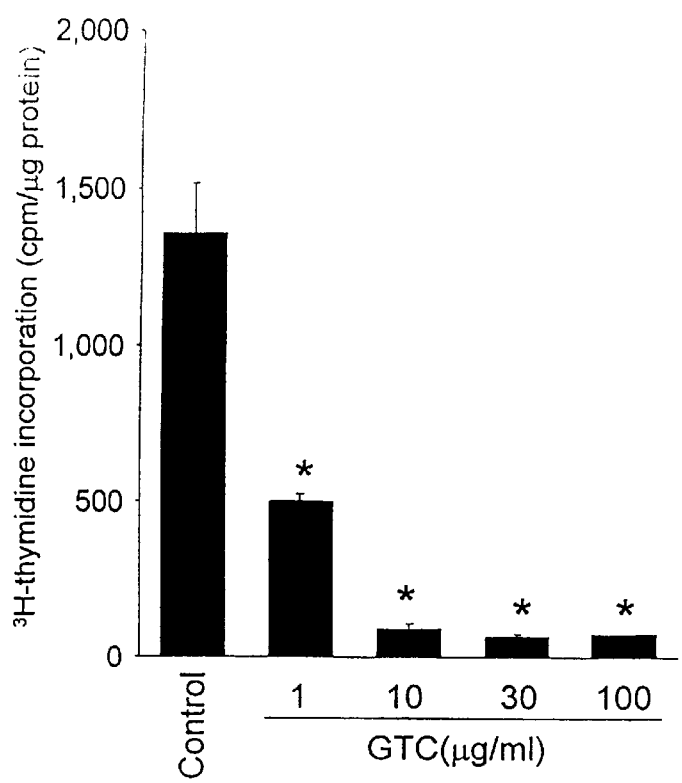
FIGS. 5A and 5B demonstrate VSMCs growth-inhibiting activity of a green tea extract in the presence and absence of platelet derived growth factor(PDGF)-BB, respectively.
Figure 5B:
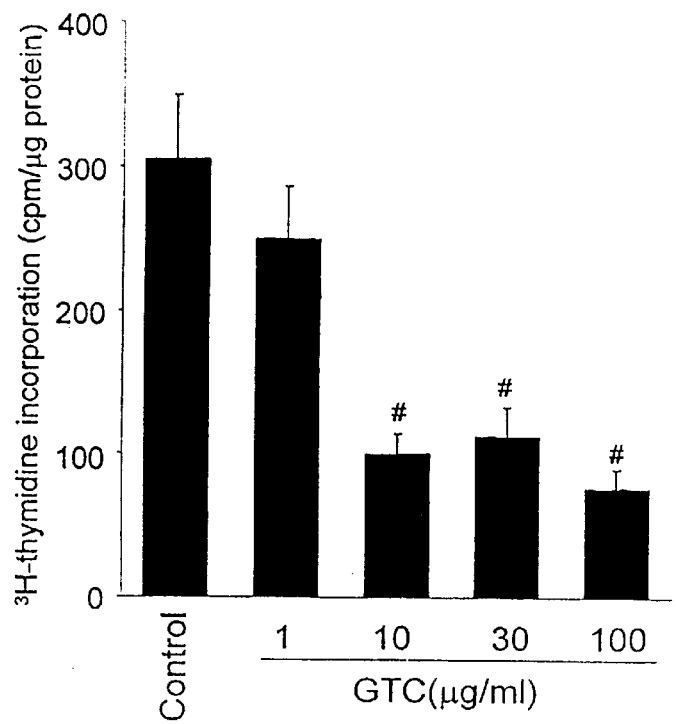

FIG. 5A shows the VSMC growth-inhibiting activity of GTC in the presence of PDGF-BB, and FIG. 5B, in the absence of PDGF-BB.

The above results first show that PDGF-BB greatly enhances the VSMC growth as the control data suggest. As can be seen from Table I and FIG. 5A, GTC inhibits the PDGF-enhanced VSMC growth in a concentration-dependent manner.

Meanwhile, Table II and FIG. 5B show GTC inhibits the VSMC growth in the absence of PDGF-BB at a concentration of 10 μg/ml or higher.

Since GTC inhibits DNA synthesis at the S stage of cell cycle, it is believed that GTC blocks conversion of $G_0$ to $G_1$, or $G_1$ to S stage.

EXAMPLE 3
Phosphorylation of Mitogen-Activated Protein Kinase

To examine the mechanism of the VSMC growth inhibition by GTC, effect of GTC on protein kinase p44/p42 activated by mitogen(Mitogen-activated protein kinase: MAPK), which is known to be essential in eukaryotic cell growth and differentiation, was determined. It is well known that the MAPK activity is increased by phosphorylation at its 204th Tyrosine residue.

The VSMC was cultured in a normal medium until confluence, and the medium was replaced by serum-free Hunger medium containing 10 or 50 μg/ml of GTC obtained in Reference Example 1. The resulting culture was incubated for 24 hours. 50 ng/ml of PDGF-BB was added thereto and kept for 5 minutes. The above procedure was repeated without GTC and PDGF-BB treatments to obtain a blank; and without GTC treatment to obtain a control. The above procedure was also repeated without PDGF-BB treatment.

The VSMC was lysed and the VSMC lysate (corresponding amount to 70 μg proteins) was subjected to SDS-PAGE. The proteins separated on the gel was transferred to a nitrocellulose membrane and the membrane was saturated with Tris buffered saline(TBS) containing 3% milk protein. A primary antibody(Promega, dilution ratio: 1:5,000) for catalytically activated $p44^{mapk}/p42^{mapk}$ whose threonine and tyrosine residues are phosphorylated, was added thereto and kept over night. The membrane was washed three times with TBS containing 0.05% Tween 20. The membrane was reacted with a horseradish peroxidase-conjugated anti-IgG secondary antibody and developed using Amersham ECL kit. Linearity of MAPK concentration-ECL signal correlation was examined using standard p42, a recombinant, activated MAPK(Upstate Biotechnology), and serially diluted artery tissue homogenate. Bands on the X-ray film were quantified using Molecular Dynamics personal laser densitometer.

Figure 6:
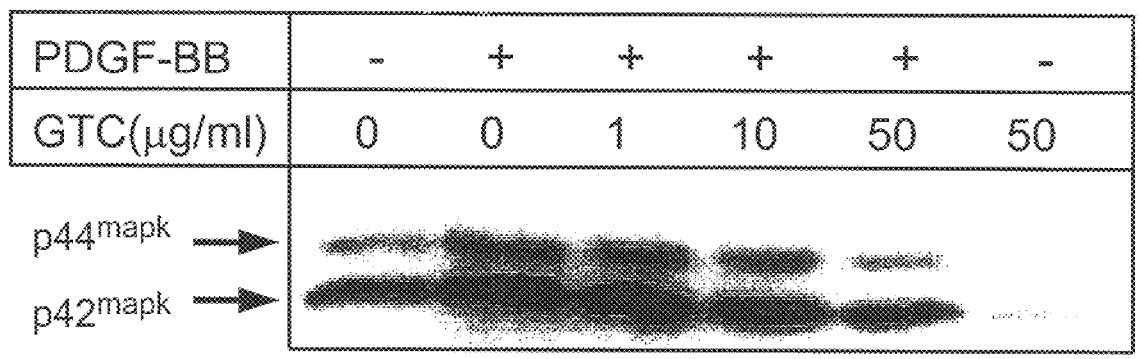
FIG. 6 summarizes the western blotting result showing green tea extract's activity for inhibiting phosphorylation of $p44^{mapk}/p42^{mapk \ in \ rat \ VSMCs}$.

FIG. 6 reproduces the western blotting result which shows the effect of GTC on phosphorylation of tyrosine(204th residue) of $p44^{mapk}/p42^{mapk}$ in rat VSMCs. As can be seen from FIG. 6, PDGF-BB-treated cells show phosphorylated $p44^{mapk}/p42^{mapk}$ bands of enhanced density as compared with the blank, whereas the GTC-pretreated cells show a concentration-dependant decrease in the phosphorylated $p44^{mapk}/p42^{mapk}$ band density. Therefore, GTC inhibits VSMC growth by inhibiting MAPK.

Figure 7:
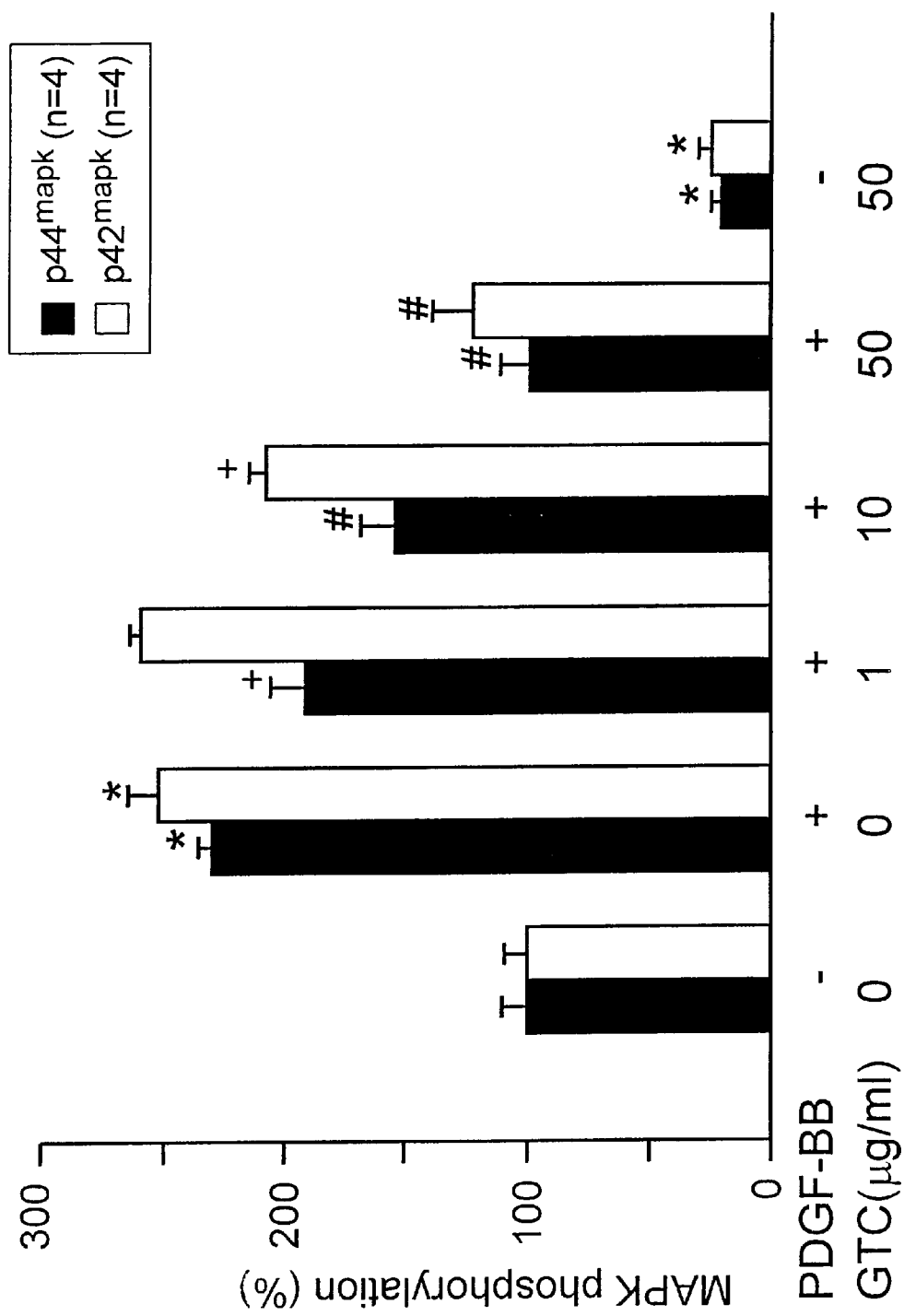
FIG. 7 quantifies the western blotting result of FIG. 6.

Densities of the bands in FIG. 6 were quantified and the results are shown in Table III and FIG. 7.

TABLE III

|  | Blank Group | Control Group | GTC-treated Group | | |
| --- | --- | --- | --- | --- | --- |
|  |  |  | 1 | 10 | 50 |
| Phosphorylation of $p44^{mapk}$ | 100 ±10.3 | 229.9 ±5.7* | 191.2 ±14.6** | 153.9 ±14.1* | 98.5 ±12.2* |
| Phosphorylation of $p42^{mapk}$ | 100 ±9.2 | 251.7 ±12.6* | 259.0 ±4.5 | 207.4 ±7.3* | 122.1 ±16.8* |

*p < 0.01
**p < 0.05

As can be seen from Table III and FIG. 7, the $p44^{mapk}$ band density increases with PDGF-BB treatment, while it decreases with GTC pretreatment. Further, the $p44^{mapk}$ band density is enhanced by PDGF-BB but suppressed when GTC treatment is carried out at a concentration of 10 μg/ml or higher.

EXAMPLE 4
Prevention of Restenosis in Injured Carotid Artery by GTC (Step 1) Operation of injured rat carotid artery Each of 13 Fisher 344 rats was subjected to intramuscular injection of 50 mg/kg ketamine and 6.7 mg/kg xylazine, and its right neck was incised to remove the common carotid artery(CCA) and its branches, i.e., external carotid artery and internal carotid artery. Microvascular clips were inserted at the starting point of CCA arteriae aorta and at the distal position of the internal carotid artery, to temporarilly block the blood stream and then the external carotid artery was incised. 2F forgarthy catheter(Baxter Healthcare Corporation, USA) was inserted through the incision site into the CCA and enlarged to a size bigger than the CCA diameter. Then, the catheter was moved back and forth five times to remove endothelial cells, and the inside of the CCA was washed with PBS. 100 μg/ml of GTC obtained in Reference Example 1 was injected to the right CCA and kept for 20 minutes to let GTC react with the injured artery wall. The microvascular clips were removed to resume the blood stream and the incision site was sutured. For a control, the above procedure was repeated using 10 rats without the GTC treatment, and their left undamaged CCAs were used as normal carotid arteries.

(Step 2) Carotid Angiography 2 weeks after the operation of Step 1, each rat was subjected to general anesthesia and its abdomen was incised. 4F vascular cannula was inserted at the abdominal arteriae aorta and positioned at the pectoral descending thoracic aorta. 4 to 6 ml of a nonionic contrast medium(Hexabrix, Schering, Germany) was injected to the rat while cineangiography was conducted. The data thus obtained were analyzed using a computer analysis system, DCI videodensitometry(Phillips, The Netherlands), to determine the diameter of the most narrow region of the damaged right CCA(Dobs) and the diameter of the normal left CCA(Dcon, 10 arbitrary unit). The degree of stenosis was represented by a percent ratio of Dobs to Dcon.

Figure 8A:
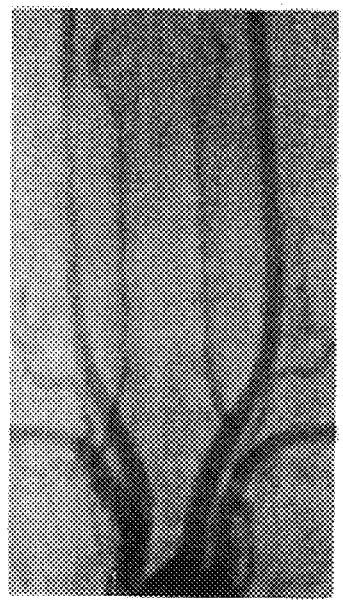
FIGS. 8A and 8B document the cineangiographs of the carotid arteries of the control group and the GTC-treated group of Example 4, respectively.
Figure 8B:
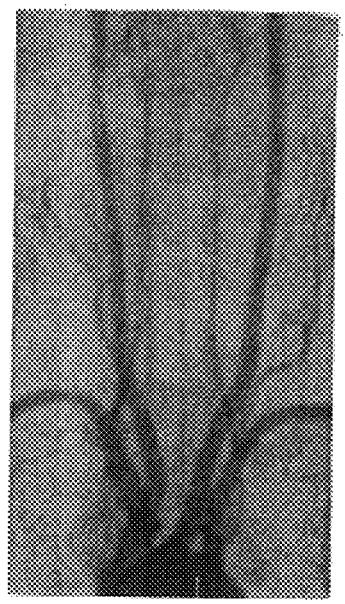

FIGS. 8A and 8B show the cineangiography results of the carotid artery of the control and the GTC-treated group, respectively. As can be seen from FIGS. 8A and 8B, the injured carotid artery of the control shows stenosis: the injured artery has a narrower inner diameter than that of the normal carotid artery, while the GTC-treated artery shows a larger inner diameter than that of the control.

When the inner diameter of the normal carotid artery is defined as 10, the most narrow inner diameter of the carotid artery of the group(n=13) treated with 100 µg/ml GTC was 5.67±1.15, while that of the control group(n=10) was higher at 4.22±1.37(p,0.05).

Figure 8C:
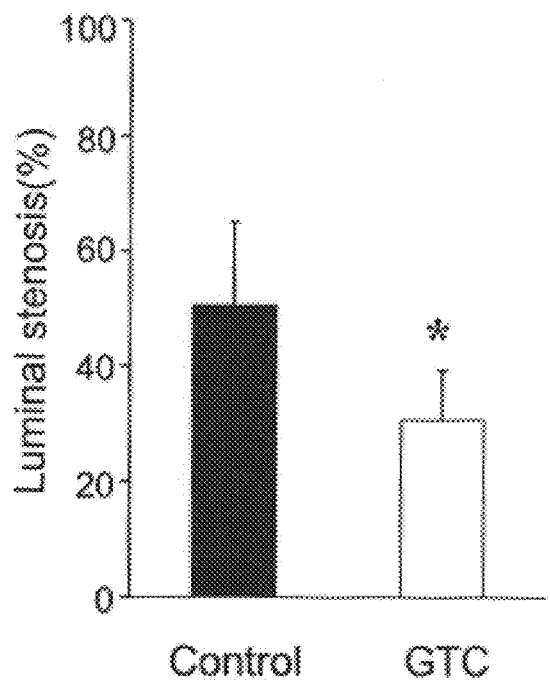
FIG. 8C: luminal stenosis values(%) of the carotid arteries of the above mentioned control and GTC-treated groups.

FIG. 8C shows that carotid artery stenosis of the control group is 50.4±13.2% while the GTC-treated group is significantly lower at 30.5±10.4%.

EXAMPLE 5
Histopathological Test

After the carotid angiography of Step 2 of Example 4, the carotid artery was perfused with 10% formalin with a pressure of 120 mmHg for 5 minutes or more, removed and then fixed in 10% formalin. A central region of the carotid artery was taken in a length of 3 mm, embedded in paraffin, cut into a series of cross sections, and then stained with hematoxylin-eosin. The cross section showing the most narrow vessel lumen was scanned and then subjected to quantitative morphometry analysis using Scion Image Analysis software(version 1.1). In this analysis, intimal wall thickness, intimal area, medial wall thickness, medial wall area, area ratio between intimal and medial area, and stenosis were used as analytic factors.

Figure 9A:
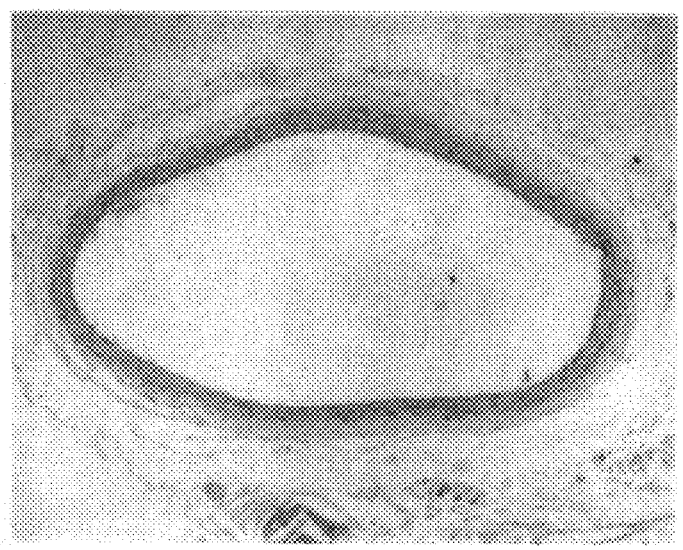
FIGS. 9A, 9B and 9C describe the photomicrographs(× 40) of the cross sections of the normal vessel lumen; the carotid artery of the control group taken 2 weeks after injury; and the carotid artery of the GTC-treated group taken 2 weeks after injury, respectively(Example 5)
Figure 9B:
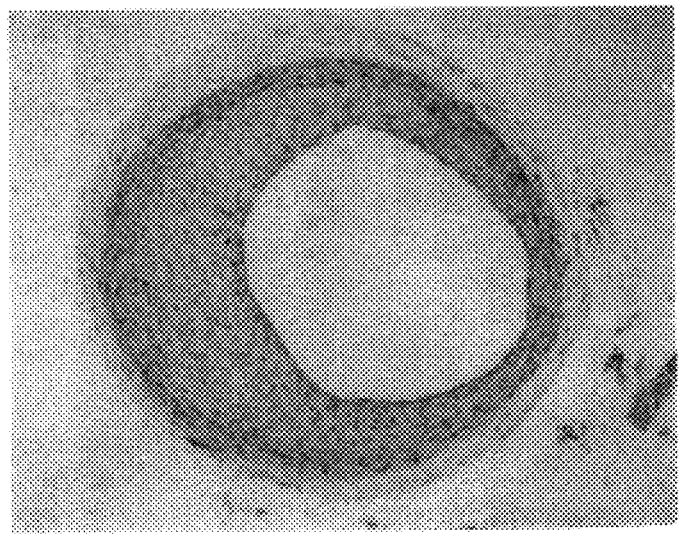
Figure 9C:
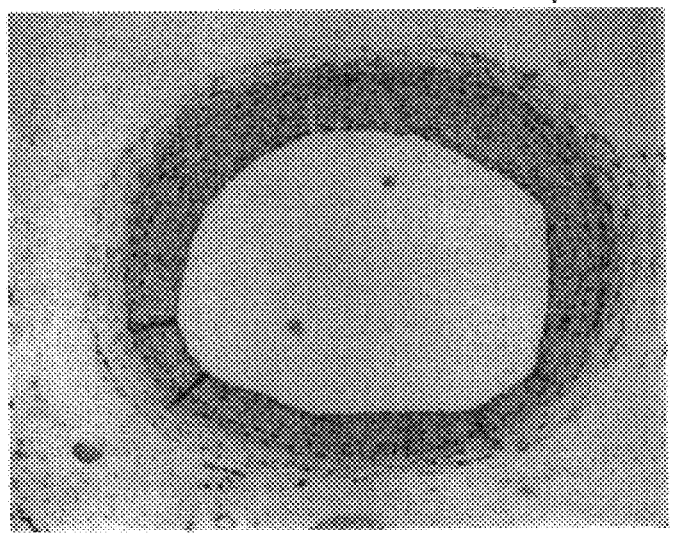

FIGS. 9A, 9B and 9C show the photomicrography results (×40) of the cross sections of the normal carotid artery, the carotid artery of the control and the carotid artery of the GTC-treated rat, respectively. As can be seen from FIGS. 9A, 9B and 9C, the control carotid artery is narrower than the normal carotid artery, exhibiting enhanced neointimal formation, whereas the artery of the GTC-treated rat is broader than the control. This suggests that GTC inhibits neointimal formation and is effective in treating restenosis.

Figure 10A:
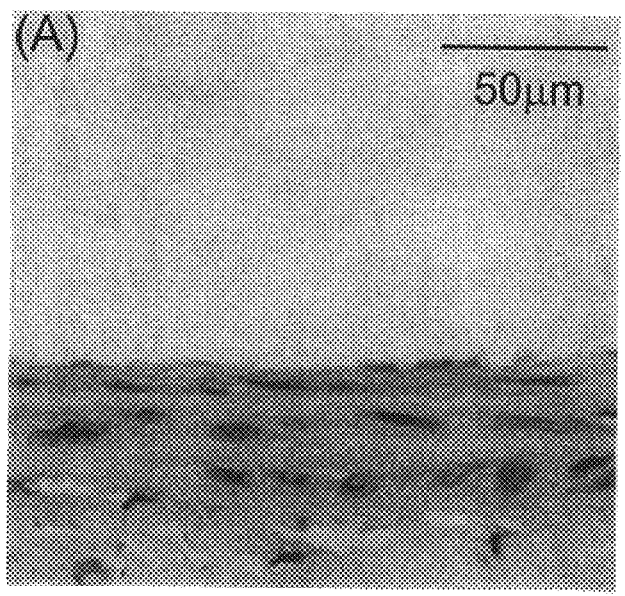
FIGS. 10A, 10B and 10C disclose the photomicrographs (×400) of the cross sections of the normal carotid artery; the carotid artery of control group taken 2 weeks after injury; the carotid artery of GTC-treated group taken from 2 weeks after injury, respectively(Example 5).
Figure 10C:
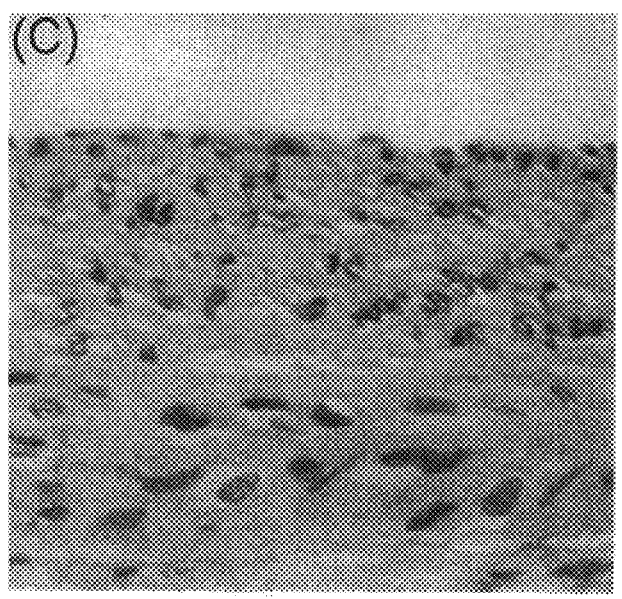
Figure 10B:
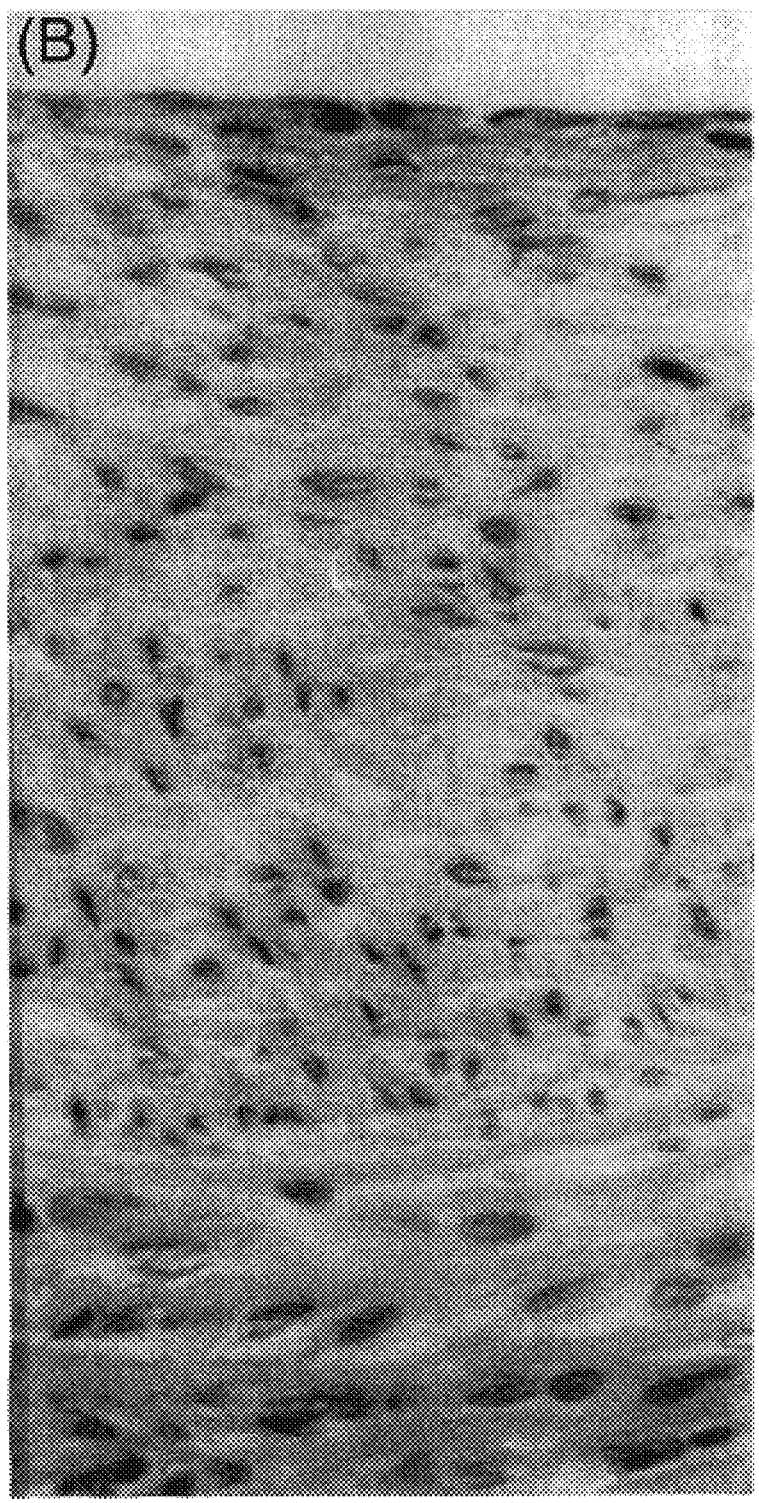

FIGS. 10A, 10B and 10C show the photomicrography results(×400) of the cross sections of the normal carotid artery, the carotid artery of the control group and the carotid artery of GTC-treated group, respectively. As can be seen from FIGS. 10A, 10B and 10C, the control shows markedly increased neointimal formation as compared with the normal carotid artery, whereas the GTC-treated does not develop severe neointimal formation. This suggests that GTC is effective in treating restenosis.

Intimal wall thickness(Tintima), medial wall thickness (Tmedia), intimal area(Aintima), area ratio between intimal and medial area(Aintima/media), and stenosis(%) were evaluated from FIGS. 10b and 10c and the results are summarized in Table IV.

TABLE IV

|  | Control Group | GTC-treated Group | P value |
|---|---|---|---|
| Tintima ($\mu$m) | 195.6 ± 56.1 | 124.4 ± 19.2 | 0.005 |
| Tmedia ($\mu$m) | 62.9 ± 7.0 | 59.5 ± 3.9 | 0.26 |
| Aintima (mm$^2$) | 0.42 ± 0.10 | 0.29 ± 0.11 | 0.03 |
| Aintima/media | 1.58 ± 0.50 | 0.92 ± 0.28 | 0.007 |
| Stenosis (%) | 46.3 ± 7.5 | 34.4 ± 11.1 | 0.03 |

As can be seen from Table IV, except for the medial wall thickness, the GTC-treated group show statistically significant differences in values in other categories as compared with the control group.

While the invention has been described with respect to the above specific embodiments, it should be recognized that various modifications and changes may be made to the invention by those skilled in the art which also fall within the scope of the invention as defined by the appended claims.

What is claimed is:

1. A method for preventing or treating coronary restenosis in a mammal which comprises administering an effective amount of a catechin thereto.

2. The method of claim 1, wherein the mammal is human.

3. The method of claim 1, wherein the catechin is selected from the group consisting of epigallocatechin-3-gallate, epigallocatechin, epicatechin-3-gallate, epicatechin, gallocatechin-3-gallate, gallocatechin, catechin and a mixture thereof.

4. The method of claim 3, wherein the mixture is an extract of green tea.

5. The method of claim 4, wherein the green tea extract has a total catechin content of 80% or more based on the weight of the green tea extract.

6. The method of claim 3, wherein the mixture has an epigallocatechin-3-gallate content of 25% or more based on the total weight of the mixture.

7. The method of claim 6, wherein the mixture has an epigallocatechin-3-gallate content ranging from 25 to 85%, epigallocatechin ranging from 6 to 20% and epicatechin-3-gallate ranging from 2 to 15%, based on the weight of the mixture.

8. The method of claim 4 or 5, wherein the green tea extract is prepared by extracting green tea with ethanol; concentrating the extract under a reduced pressure; diluting the concentrate with water; centrifuging the diluted solution to obtain a supernatant by removing solid materials; washing the supernatant with chloroform to obtain an aqueous layer; extracting the aqueous layer with an organic solvent; and removing the organic solvent.

9. The method of any one of claims 1 to 7, wherein the coronary restenosis is caused by angioplasty of coronary artery using a balloon, stent enthesis, coronary artery bypass graft or arteriovenous shunt.

* * * * *